United States Patent [19]

Kollmeyer

[11] Patent Number: 4,551,447
[45] Date of Patent: Nov. 5, 1985

[54] BETA-IMIDAZOLYL-ALPHA-(TRI-FLUOROMETHYL)ETHENYL PHOSPHATES AND INSECTICIDAL AND MITICIDAL USE

[75] Inventor: Willy D. Kollmeyer, Modesto, Calif.

[73] Assignee: Shell Oil Company, Houston, Tex.

[21] Appl. No.: 726,575

[22] Filed: Apr. 24, 1985

[51] Int. Cl.$^4$ .................. A01N 57/16; C07F 9/65
[52] U.S. Cl. .................... 514/94; 548/119; 548/342
[58] Field of Search ............ 548/119; 514/94

[56] References Cited

FOREIGN PATENT DOCUMENTS 3105223 9/1982 Fed. Rep. of Germany .

Primary Examiner—Richard L. Raymond

[57] ABSTRACT

Novel compounds of the formula

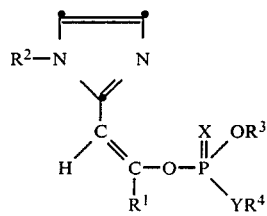

wherein $R^1$ is (halo)alkyl or optionally substituted phenyl; $R^2$ is H, or alkyl; $R^3$ and $R^4$ each is alkyl; and X and Y each is O or S, are useful as insecticides and miticides.

11 Claims, No Drawings

BETA-IMIDAZOLYL-ALPHA-(TRIFLUOROMETHYL)ETHENYL PHOSPHATES AND INSECTICIDAL AND MITICIDAL USE

BACKGROUND OF THE INVENTION

Field of the Invention

The present invention relates to novel beta-imidazolyl-alpha-(trifluoromethyl)ethenyl phosphates, intermediates therefore, their use as pesticides, to pesticidal compositions of these novel compounds and to the preparation of certain intermediates.

SUMMARY OF THE INVENTION

The present invention is directed to novel compounds of the formula I

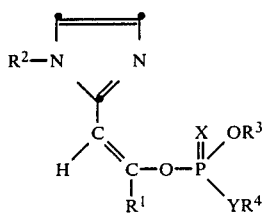

wherein $R^1$ is an alkyl group containing from 1 to 6 carbon atoms optionally substituted by one or more halogen atoms and having no alpha hydrogen atoms; a phenyl group optionally substituted by one or more halogen atoms or alkyl or alkoxy groups containing 1 to 2 carbon atoms each optionally substituted by one or more halogen atoms; $R^2$ is a hydrogen atom, or an alkyl group containing 1 to 4 carbon atoms; $R^3$ and $R^4$ each independently is an alkyl group containing 1 to 6 carbon atoms; and X and Y each independently is an oxygen or sulfur atom.

Non limiting embodiments of the compounds of formula I of the invention include:
Phosphorothioic Acid, O-ethyl S-propyl O-[1-(trifluoromethyl)-2-(1-methyl-1H-imidazol-2-yl)ethenyl] ester,
Phosphorothioic Acid, O,O-diethyl O-[1-(trifluoromethyl)-2-(1-methyl-1H-imidazol-2-yl)ethenyl] ester,
Phosphorothioic Acid, O-ethyl O-[2-(1-methyl-1H-imidazol-2-yl)-1-phenylethenyl] S-propyl ester,
Phosphorothioic Acid, O,O-diethyl O-[2-(1-methyl-1H-imidazol-2-yl)-1- phenylethenyl] ester,
Phosphoric Acid, O-[1-(2-chlorophenyl)-2-(1-methyl-1H-imidazol-2-yl)-ethenyl] O,O-diethyl ester,
Phosphoric Acid, O-[1-(3-chlorophenyl)-2-(1-methyl-1H-imidazol-2-yl)-ethenyl] O,O-diethyl ester,
Phosphoric Acid, O-[1-(4-chlorophenyl)-2-(1-methyl-1H-imidazol-2-yl)-ethenyl] O,O-diethyl ester,
Phosphoric Acid, O-[1-(2-chloro-6-fluorophenyl)-2-(1-methyl-1H-imidazol-2-yl)ethenyl] O,O-diethyl ester,
Phosphoric Acid, O-[1-(2,6-difluorophenyl)-2-(1-methyl-1H-imidazol-2-yl)ethenyl] O,O-diethyl ester,
Phosphoric Acid, O-[1-(2,4-chlorophenyl)-2-(1-methyl-1H-imidazol-2-yl)ethenyl] O,O-diethyl ester,
Phosphoric Acid, O,O-diethyl O-[1-(2,4,5-trichlorophenyl)-2-(1-methyl-1H-imidazol-2-yl)ethenyl] ester, and the corresponding compounds wherein $R^1$ is methyl or the like; $R^2$ is hydrogen or the like; and $R^3$ and $R^4$ are methyl, ethyl or the like.

In one embodiment of the invention, $R^1$ is trifluoromethyl, phenyl or phenyl substituted by one or more atoms of chlorine, fluorine or bromine. Preferably, $R^1$ is trifluoromethyl or phenyl.

In another embodiment of the invention, $R^2$, $R^3$ and $R^4$ each independently is an alkyl group containing 1 to 4 carbon atoms. Preferably, $R^2$ is a methyl group. Preferably, $R^3$ and $R^4$ each is an ethyl group.

In another embodiment of the invention, X and Y each is an oxygen atom.

The compounds of formula I of the present invention are capable of existing as E and/or Z isomer forms because of the pressure of the vinyl carbon-carbon double bond bearing the imidazole, $R^1$, and O-phosphate substituents. Likewise, the intermediates of formula II of the present invention are capable of existing in various tautomeric forms (enol, enone and ketone). When $R^1$ is trifluoromethyl, the enol form shown in a stable form of the compounds of the invention. The present invention contemplates all of the insecticidally active forms of the isomers described above or any of the tautomers and isomers that are intermediate thereto. This includes single forms or natural or artificially created mixtures of these forms.

The compounds of formula I are prepared by treating appropriately $R^1$ and $R^2$ substituted imidazoles II

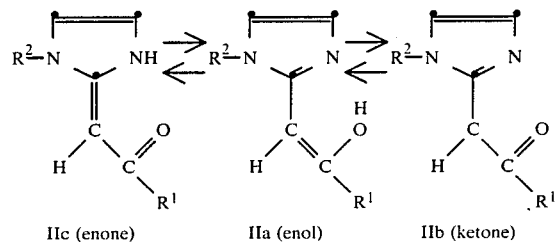

IIc (enone)    IIa (enol)    IIb (ketone)

with a dialkyl chlorophosphate

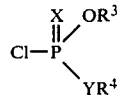

in the presence of a tertiary-amine halide acceptor, such as triethylamine, in an inert solvent, such as ether, to yield the desired products, usually as crystalline solids, which can be recovered by conventional techniques.

The appropriate $R^1$ and $R^2$ substituted imidazoles are prepared by conventional techniques known in the art from readily available 1-($R^2$-(un)substituted)-2-methylimidazoles. For example, as described in J.C.S. Chem. Commun., 1974, 36, and J. Org. Chem., 40, 252 (1975), treatment of 1,2-dimethylimidazole with benzoyl chloride in the presence of triethylamine and acetonitrile gave a carbon, oxygen-bis-acylated intermediate, which on treatment with aqueous HCl followed by sodium hydroxide gave the compound of formula IIb in which $R^1$ was phenyl and $R^2$ was methyl.

The intermediates II wherein $R^1$ is trifluoromethyl are novel and are prepared by a novel process of the invention which comprises treating a 2-methylimidazole substituted at the 1-position by a hydrogen atom or an alkyl group with trifluoroacetic anhydride. The reaction is preferably conducted in the presence of a halide acceptor, such as triethylamine or the like, and also, preferably in the presence of an inert solvent, such as acetonitrile. For example, treatment of 1,2-dimethylimidazole with trifluoroacetic anhydride in the presence of triethylamine and acetonitrile gives a novel carbonbis-acylated intermediate of formula III,

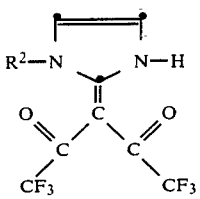

III which upon undergoing an acid-catalyzed retroaldol process in ethanol gives the compound of formula IId

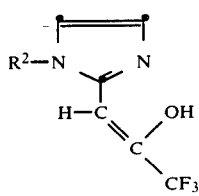

IId in which $R^2$ is a hydrogen atom or an alkyl group containing 1 to 4 carbon atoms. The products of each step are usually crystalline and are recovered by conventional techniques known in the art.

ILLUSTRATIVE EMBODIMENTS

The invention is illustrated by the following embodiments describing the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analysis as necessary.

EMBODIMENT 1

3-(2,3-Dihydro-1-methyl-1H-imidazol-2-ylidene)-1,1,1,5,5,5-hexafluoro-2,4-pentanedione An ice-cooled and stirred solution of 9.61 g 1,2-dimethylimidazole, 22.0 g triethylamine and 100 ml dry acetonitrile was treated dropwise with 42.0 g trifluoroacetic anhydride with exclusion of moisture. After stirring at ambient temperature for 4 hours, the solvent was stripped and the residue was stirred and diluted dropwise with 400 ml cold water. The crystalline precipitate, after filtration and drying, weighed 23.1 g, m.p. 180° C. (resolidification), 200°–202° C. A 100 mg test portion was recrystallized from acetonepetroleum ether to give a sample with unchanged melting point.

EMBODIMENT 2

1-(Trifluoromethyl)-2-(1-methyl-1H-imidazol-2-yl)ethanol

A solution of 8.64 g of the product of Embodiment 1 above, 0.25 g concentrated sulfuric acid, and 100 ml ethanol was refluxed for 6 hours and then stripped. The residue was taken up in 250 ml methylene chloride and decanted from a small amount of insoluble solid. The organic layer was washed with 50 ml 10% aqueous sodium bicarbonate. The basic layer was extracted twice with additional methylene chloride. All of the organic layers are combined, dried ($MgSO_4$), and evaporated to give a quantitative yield of crude white product, m.p. 145°–146° C. Recrystallization from chloroform-petroleum ether afforded 4.52 g, of the desired product as white crystals, m.p. 146°–148° C.

EMBODIMENT 3

Phosphoric Acid, Diethyl 1-(Trifluoromethyl)-2-(1-methyl-1H-imidazol-2-yl)ethenyl Ester Diethyl chlorophosphate (1.90 g) was added to a stirred mixture of 1.94 g of the product of Embodiment 2 above and 1.13 g of triethylamine in 25 ml dry ether at room temperature with exclusion of ambient atmosphere (Argon). The mixture was heated at reflux for 3.5 hours, cooled, and filtered. Evaporation of solvent from the filtrate gave a semisolid that was recrystallized from ether-pentane to give 2.70 g of light orange product with m.p. 54°–64° C.

EMBODIMENT 4

Alpha-((1-methyl-1H-imidazol-2-yl)methylene)benzenemethanol, Benzoate

With exclusion of moisture, an ice-cooled and stirred solution of 12.1 g 1,2-dimethylimidazole, 27.7 g triethylamine, and 200 ml acetonitrile was treated with 35.1 g benzoyl chloride. Addition time was 30 min. After another 90 minutes at room temperature, 125 ml of acetonitrile was stripped (50° C., water-aspirator pressure) and the residue was diluted with 200 ml ether. The resulting slurry was stirred and treated dropwise with 400 ml water. The crystalline product was filtered, washed twice with water and once with ice-cold isopropyl alcohol. The yield was 30.9 g of the desired product; m.p. 139°–140° C. (literature m.p. 140° C.).

EMBODIMENT 5

2-(1-Methyl-1H-imidazol-2-yl)-1-phenylethanone

A mixture of 15.2 g of the product of Embodiment 4 above and 100 ml 3N hydrochloric acid was heated at reflux for 1 hour and then cooled by pouring onto ice. The precipitated benzoic acid was removed by extraction with methylene chloride (3×75 ml). The aqueous acid layer was neutralized by addition of 26.0 g sodium bicarbonate in small portions. White crystalline product slowly deposited from the neutralized solution. After 30 minutes at room temperature, the crystals were filtered, washed with water, and dried in vacuo at room temperature. The yield was 6.95 g of the desired product; m.p. 98°–100° C. (literature m.p. 101° C.).

EMBODIMENT 6

Phosphoric Acid, Diethyl 2-(1-Methyl-1H-imidazol-2-yl)-1-phenylethenyl Ester

A mixture of 1.50 g of the product of Embodiment 5 above, 0.80 g of triethylamine and 1.73 g of diethyl chlorophosphate in 50 ml dry ether was stirred at room temperature for 3 days with exclusion of moisture (Argon). The mixture was diluted with 200 ml methylene chloride and washed with water (3×50 ml). The organic phase was dried ($MgSO_4$) and concentrated to yield 2.51 g of a gray solid. A sample recrystallized from methylene chloride-hexane gave the desired product; m.p. 111°–114° C.

The compounds of the invention have been found to be toxic to insects and mite pests.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides —i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0.1% by weight of additives such as stabilizers, slow release modifiers and binding agents. Emulsifiable concentrates usually contain, in addition to the solvent and, when necessary, cosolvent, 10-15% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient. The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Adult female two-spotted spider mites (*Tetranychus urticae* (Koch)) were tested by placing 50–75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

In each set of tests, identical tests were conducted using Parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index | | |
| --- | --- | --- | --- |
|  | House-fly | Pea Aphid | Spider Mite |
| 3 | 26K | 66K | 295 |
| 6 | 13 | 7 | 184 |

K means knockdown activity.

What is claimed is:

1. A compound of the formula I

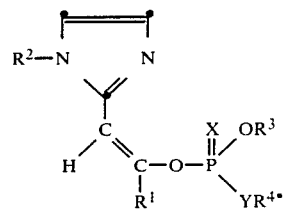

wherein $R^1$ is an alkyl group containing from 1 to 6 carbon atoms optionally substituted by one or more halogen atoms, a phenyl group optionally substituted by one or more halogen atoms or alkyl or alkoxy groups containing 1 to 2 carbon atoms each optionally substituted by one or more halogen atoms; $R^2$ is a hydrogen atom, or an alkyl group containing 1 to 4 carbon atoms; $R^3$ and $R^4$ each independently is an alkyl group containing 1 to 6 carbon atoms; and X and Y each independently is an oxygen or sulfur atom.

2. A compound according to claim 1 wherein $R^1$ is trifluoromethyl, phenyl or phenyl substituted by one or more atoms of chlorine, fluorine or bromine.

3. A compound according to claim 1 wherein $R^2$, $R^3$ and $R^4$ each independently is an alkyl group containing 1 to 4 carbon atoms.

4. A compound according to claim 3 wherein $R^1$ is trifluoromethyl or phenyl.

5. A compound according to claim 4 wherein X and Y each is an oxygen atom.

6. A compound according to claim 5 wherein $R^3$ and $R^4$ each is an ethyl group.

7. A compound according to claim 6 wherein $R^2$ is a methyl group.

8. A compound according to claim 7 wherein $R^1$ is trifluoromethyl.

9. A compound according to claim 7 wherein $R^1$ is a phenyl group.

10. An insecticidal composition comprising an insecticidally or miticidally effective amount of a compound according to claim 1 and at least one surface active agent or carrier.

11. A method of combatting insect pests at a locus which comprises applying to the locus or the pests an insecticidally or miticidally effective amount of a compound according to claim 1.

* * * * *